US011107100B2

(12) United States Patent
Baughman et al.

(10) Patent No.: US 11,107,100 B2
(45) Date of Patent: Aug. 31, 2021

(54) DISTRIBUTING COMPUTATIONAL WORKLOAD ACCORDING TO TENSOR OPTIMIZATION

(71) Applicant: International Business Machines Corporation, Armonk, NY (US)

(72) Inventors: Aaron K. Baughman, Cary, NC (US); Gray Cannon, Miami, FL (US); Micah Forster, Round Rock, TX (US); Shikhar Kwatra, Durham, NC (US)

(73) Assignee: International Business Machines Corporation, Armonk, NY (US)

( * ) Notice: Subject to any disclaimer, the term of this patent is extended or adjusted under 35 U.S.C. 154(b) by 111 days.

(21) Appl. No.: 16/536,425

(22) Filed: Aug. 9, 2019

(65) Prior Publication Data

US 2021/0042773 A1    Feb. 11, 2021

(51) Int. Cl.
*G06Q 30/02* (2012.01)
*G16H 50/30* (2018.01)
*G06Q 10/06* (2012.01)

(52) U.S. Cl.
CPC ..... *G06Q 30/0206* (2013.01); *G06Q 10/0635* (2013.01); *G16H 50/30* (2018.01)

(58) Field of Classification Search
CPC . G06Q 30/0206; G06Q 10/0635; G16H 50/30
See application file for complete search history.

(56) References Cited

U.S. PATENT DOCUMENTS

| | | | |
|---|---|---|---|
| 6,271,856 B1 | 8/2001 | Krishnamurthy | |
| 6,448,968 B1 | 9/2002 | Pfister | |
| 7,752,064 B2 | 7/2010 | Kauffman | |
| 8,340,794 B1* | 12/2012 | Trdinich | A63F 13/46 700/91 |
| 8,793,381 B2 | 7/2014 | Baughman | |
| 2009/0150236 A1* | 6/2009 | Price | G06Q 30/02 705/14.13 |
| 2010/0036884 A1* | 2/2010 | Brown | G06Q 30/00 706/21 |
| 2010/0131624 A1* | 5/2010 | Ferris | G06F 9/5072 709/221 |
| 2010/0306379 A1* | 12/2010 | Ferris | H04L 41/5006 709/226 |
| 2016/0239916 A1* | 8/2016 | Korn | G06Q 40/06 |
| 2017/0344906 A1 | 11/2017 | Wang | |

(Continued)

FOREIGN PATENT DOCUMENTS

| | | |
|---|---|---|
| CN | 105654110 A | 6/2016 |
| CN | 105913085 A | 8/2016 |

OTHER PUBLICATIONS

"The Global Network Optimization Services Market size is expected to reach $9.6 billion by 2023", News Provided by ReportBuyer, Jan. 5, 2018, 3 pages, <https://www.prnewswire.com/news-releases/the-global-network-optimization-services-market-size-is-expected-to-reach-96-billion-by-2023-3005781.html>.

(Continued)

*Primary Examiner* — Sujay Koneru
(74) *Attorney, Agent, or Firm* — David K. Mattheis; Maeve M. Carpenter (57) ABSTRACT

Optimizing market assets using tensor optimization across cloud and edge resources by generating a tensor space associated with market assets, calculating matrices associated with the tensor space according to market asset correlations, determining market asset allocation opportunities, and suggesting market asset allocations according to a user risk assessment.

20 Claims, 6 Drawing Sheets

(56) References Cited

U.S. PATENT DOCUMENTS

| | | | | |
|---|---|---|---|---|
| 2018/0152361 | A1* | 5/2018 | Chu | H04L 67/02 |
| 2018/0158078 | A1* | 6/2018 | Hsieh | G06N 20/00 |
| 2018/0183585 | A1* | 6/2018 | Kent | H04L 9/0852 |
| 2018/0248941 | A1* | 8/2018 | Naik | H04L 41/0896 |
| 2018/0300124 | A1* | 10/2018 | Malladi | G05B 15/02 |
| 2018/0301223 | A1* | 10/2018 | Alter | G16B 20/00 |
| 2019/0014487 | A1 | 1/2019 | Yang | |
| 2019/0019119 | A1* | 1/2019 | Lucas | G06Q 40/06 |
| 2019/0347790 | A1* | 11/2019 | Lee | G06T 7/0012 |
| 2020/0073717 | A1* | 3/2020 | Hari | G06F 9/5027 |
| 2020/0151815 | A1* | 5/2020 | Whitfield | G06Q 50/01 |
| 2020/0167196 | A1* | 5/2020 | Smith | H04L 47/781 |
| 2020/0241928 | A1* | 7/2020 | Senevirathne | G06F 9/5005 |
| 2020/0250717 | A1* | 8/2020 | Todd | G06F 16/9014 |
| 2020/0264914 | A1* | 8/2020 | Dasgupta | H04W 76/10 |
| 2020/0286180 | A1* | 9/2020 | Mauck, Jr. | G06F 16/248 |
| 2020/0327371 | A1* | 10/2020 | Sharma | G06N 20/00 |
| 2020/0336376 | A1* | 10/2020 | Mahdi | H04L 41/0823 |
| 2020/0348662 | A1* | 11/2020 | Cella | G05B 23/024 |
| 2020/0382445 | A1* | 12/2020 | Calmon | H04L 47/827 |

OTHER PUBLICATIONS

Edge et al., "Security Education on a Budget: Getting the Most "Bang for the Buck" with Limited Time and Resources", InfoSecCD'10, Oct. 1-2, 2010, Kennesaw, GA, USA, pp. 29-35, Copyright © 2010 ACM 978-1-60558-661-8/10/10.

Edge, Stephen William, "An Adaptive Timeout Algorithm for Retransmission Across a Packet Switching Network", Department of Computer Science, University College London, pp. 248-255, © 1984 ACM.

Han et al., "A Real-Time Augmented-Reality System for Sports Broadcast Video Enhancement", MM'07, Sep. 23-28, 2007, Augsburg, Bavaria, Germany, pp. 337-340, Copyright 2007 ACM 978-1-59593-701-8/07/0009.

Liu et al., "A Tensor-Based Holistic Edge Computing Optimization Framework for Internet of Things", Edge Computing for the Internet of Things, IEEE Network, Jan./Feb. 2018, pp. 88-95, Digital Object Identifier: 10.1109/MNET.2018.1700193.

Mell et al., "The NIST Definition of Cloud Computing", Recommendations of the National Institute of Standards and Technology, Special Publication 800-145, Sep. 2011, 7 pages.

Wang et al., "A Tensor-Based Big-Data-Driven Routing Recommendation Approach for Heterogeneous Networks", Space and Terrestrial Integrated Network: Emerging Research Advances, Prospects, and Challenges, IEEE Network, Jan./Feb. 2019, pp. 64-69, Digital Object Identifier: 10.1109/MNET.2018.1800192.

Wang et al., "A Cloud-Edge Computing Framework for Cyber-Physical-Social Services", Human-Driven Edge Computing and Communication, IEEE Communications Magazine, Nov. 2017, pp. 80-85, Digital Object Identifier: 10.1109/MCOM.2017.1700360.

* cited by examiner

DISTRIBUTING COMPUTATIONAL WORKLOAD ACCORDING TO TENSOR OPTIMIZATION

BACKGROUND

The disclosure relates generally to distributing computing workloads across edge devices, edge servers and cloud resources. The disclosure relates particularly to optimizing market assets using tensor optimization across cloud and edge resources.

E-commerce and digital gaming market spaces provide users the opportunity to engage with others and to trade assets in a marketplace. All users seek to maximize the value of the overall asset portfolio through the trading of assets.

Cloud computing provides users access to computing resources which can be scaled to match the computing needs of the user. Edge computing provides local computing resources which offer the additional benefits of reduced latency, more bandwidth as well as greater autonomy and privacy.

SUMMARY

Aspects of the invention disclose methods, systems and computer readable media associated with optimizing market asset trades using tensor optimization across cloud and edge resources by generating a tensor space associated with market assets and market users, calculating matrices associated with the tensor space according to market asset correlations, determining market asset allocation opportunities, and suggesting market asset allocations according to a market user risk assessment.

DETAILED DESCRIPTION

The characterization of asset portfolio elements relative to other market assets for the purpose of optimizing asset trading, is a large combinatorial problem. This problem has been addressed by bounding a search space and limiting the effort to searching for similar assets or similar users. The inventions disclosed herein utilize tensor spaces and correlation indices associated with positive outcomes and historical data for incidence occurrence. The disclosed inventions further incorporate user risk-tolerance based upon biometric data to increase the utility of the asset trading opportunities.

The disclosed inventions can require significant computational resources. The allocation of actions within the disclosed inventions is distributed according to the needs associated with the current activity. Computationally intensive tensor space and matrix calculations, for millions or billions of data rows, are allocated to cloud computing resources. Less computationally intensive activities associated with optimizing tensors in sparse matrices, are allocated to edge resources—edge servers or edge devices—depending upon the tensor and matrix sizes and density, the location and quantity of data, as well as the edge capacity (bandwidth) available for the optimization activities.

The edge cloud provides a decentralized mechanism to offer users computing resources and capabilities beyond those of their mobile device. A personal edge cloud provides an opportunity to store and process data without giving up control over the data. Use of edge cloud resources provides the user additional capacity to perform data analytics on their data across multiple user experiences with different providers. The edge cloud also reduces performance latency issues as the resources tend to be closer to the user's location.

Edge cloud resources are locally available network resources accessible by user devices using wireless and wired connections. Users can increase available computing resources by running user applications using edge cloud resources. Users typically do not own the edge cloud resources but do control the applications running on the resources and the data processed and stored there.

The disclosed inventions are applicable to marketplaces where assets are traded. Digital fantasy sports leagues are an example of one such marketplace. Without intending to limit the inventions, the methods and systems of the invention are described using a fantasy football league as an example.

In an embodiment, a rate of suggestion for trading assets is determined according to user engagement, data derived from the user's record of interactions with the marketplace, their historic asset trading frequency, as well as user need indicated by the current performance of the user's team and the individual players of the user's team. Underperforming players/assets can be seen as an indication that a trade at the player's position is needed. User subscriptions (e.g., how many players a user has chosen to actively follow) can also be used as an indicator of engagement. A user watching more players is seen as more engaged and more amenable to a proposed trade. Player trading frequency—how often the players on a user's team are traded—can also be considered in determining the user's need and the rate of suggested trades.

Low user engagement, together with low team performance, can indicate a user who is disengaged due to the low performance and who is amenable to a trade in the hope of raising performance, and therefore, engagement as well.

Engagement can consider eye tracking data from a user facing camera, how often the user engages relevant software, the trading app, as well as league and player performance tracking software. The duration of engagement, as well as active participation, mouse movement, keyboard entries, and touchscreen interactions, can all be tracked as indicators of user engagement. This data is evaluated using iterative methods, including the Runge-Kutta method to determine the optimal rate at which asset trades should be suggested for each system user.

In an embodiment, tensor spaces for market assets are generated. In this embodiment, a tensor space correlating fantasy football players with fantasy football teams having a winning outcome (player tensors) is generated. In an embodiment, the player tensor for each player includes additional information about the player such as player ranking, playing history—high school, college and professional playing history—injury history, performance statistics, physical statistics, as well as data associated with a user's current need relative to the player's position. Player ranking can be an external input, providing an indication of the weighting or ranking of players according to the trading community or other group. In an embodiment, weighting is associated with the market ranking of the asset. The player ranking can be subjectively based upon community member opinions, or objectively based upon a comparison of performance statistics. Player tensors are captured along a performance timeline such that the tensor space includes the player's performance history over time. The tensors for each player over time are combined into the player tensor space. The player tensor space enables the evaluation of correlations between player independent variables.

A user tensor space of user-based tensors is also generated, including user team win/loss performance over time, user team composition, user biometric data, as described above, as well as user historic trading frequency, user subscription data, and team need data for each user. The user tensors are also taken along a timeline resulting in a user tensor space which enables correlation among the values of the user independent variables to evaluate user risk tolerance in view of team needs, team performance, and current user biometric data.

The player and user tensor spaces are combined yielding a full correlation tensor space enabling the evaluation of correlations among all of the player and user independent variables. The calculation of the full correlation tensor space is computationally intensive as millions of rows and columns can be involved in the respective and combined tensor spaces. Computation of the matrices associated with the full correlation tensor is allocated to cloud resources due to the magnitude of the computational problem.

In an embodiment, the full correlation tensor is evaluated using Gaussian Mix models (GMM) to show the clustering of the tensor space data. The GMM maps the data into a set of data classes (clusters) reflecting the correlations of the independent variables of the tensor space, and defines a probability, or confidence level, for each data point with regard to the different classes/clusters. A higher probability indicates a stronger correlation, and therefore higher level of confidence, that the data correlates with the class. The inverse of this probability is defined as the sparseness of the data point, with a higher sparseness indicating a low probability of correlation. In an embodiment, sparseness is associated with the market class of the data. The GMM for the fantasy football league allows users to map the correlation of independent variable input values with mapped classes. A full GMM is generated for the combined full player and user tensors. Full GMM generation is also computationally intensive and must be performed using cloud resources.

The player and user tensor spaces can be combined in a manner where limited combinations of players are considered. For example, for each user's team, the correlation of trading a single position player for available players at the same position, with increasing the probability of the team winning, can be evaluated using a limited tensor space. The correlation of trading pairs of players with winning outcomes can also be evaluated using the limited combination correlation tensor spaces. The calculation of combination tensor spaces across all league users and all potential players is also computationally intensive and is also allocated to cloud resources. GMM evaluations of the full and combination tensor spaces require the allocation of the tasks to cloud resources due to their greater capacity.

The GMMs of the combination tensor spaces can be used to compare how well players, and combinations of players, correlate with winning outcomes. The sets of players and combinations of players can be ranked according to this correlation and its inverse (sparseness) to support the comparison. Players and combinations of players having similar or equal rankings are considered trading candidates as their impact on winning outcomes appears to be equivalent. Such combinations are then considered in real time in conjunction with the current team make-up of users as described below.

After the generalized full and combination tensor spaces and associated GMM have been calculated for the set of traders (users) and assets (players), the GMMs are used in real time to identify trading opportunities. These calculations are less computationally intensive and are allocated to edge cloud resources. In an embodiment, the assets of a trader are considered in terms of their performance and the user's current state mapped to the player, user, and full tensor space GMMs to identify needs and users amenable to a proposed trade.

In this embodiment, each asset's current performance and other data are correlated with winning outcomes, trading frequency, and average player performance at the individual player's position to identify players to consider as available for trading. In an embodiment, all players on the user's current team are considered as available for trading, both alone and in combinations. The current values of the user's and the user's current player's independent variables are mapped to the desired outputs using the GMMs of the full tensor space and the combination tensor space. This mapping yields an output including the player's ranking (weight), as well as a probability, or confidence level, of how well the independent variable data correlates with the output (user's winning team outcomes).

In an embodiment, sparseness is evaluated together with asset weight to identify anomalies in the set of assets. These anomalies include assets which are highly weighted but sparse, or poorly correlated with winning outcomes. Such anomalous assets represent good trading opportunities.

As trading requires at least two trading parties, the method evaluates the current state of each user's team and compares the evaluations across all the teams. The comparison considers the current weighting of players, and combinations of players, as well as the comparison of each player's performance to other players, and the player and player combination's correlation with winning outcomes for the users compared to other team members, as provided by comparing the combination tensors GMMs. Pairs of assets are evaluated according to their combined weight and combined correlation to winning outcomes as a pair, and in combination with a user's other team members. The system also considers each user's current needs, risk tolerance, and receptivity to suggested trades as determined by mapping the user's current state to trading risk tolerance using the GMM of the full tensor space.

In an embodiment, the system matches underperforming assets of one user with underperforming assets of a second user to identify opportunities where trading the assets will raise the likelihood of both user's teams having a winning outcome. In this embodiment, a set of possible trading combinations of assets and users is determined from the current state of the set of users and the associated teams (asset portfolios). The risk tolerance of the users is then considered in addition to the determined set of trading possibilities. Trades are suggested to users in a descending ranked order from those pairs of users currently most likely to agree to a trade to those pairs of users least likely to agree to a proposed trade.

In this embodiment, the matching of assets is achieved by comparing GMM mappings of different combinations of assets using the combination tensor space GMMs. As an example, player A, of User 1's team is identified as a trade prospect due to a low current correlation to winning outcomes for User 1's team. The system compares trading alternatives for player A, using the combination tensor space GMMs, and determines that trading player A, for player O, of User 2's team would increase the likelihood of a winning outcome for User 1, but not for User 2. The weighting of player A, also exceeds the weighting of player O. These factors limit the likelihood that User 2 would accept the proposed trade. The system further evaluates the combination of trading User 1's players A and B, for User 2's players O, and P, using the combination tensor space GMMs. The system determines that these pairs of players have equal weights and that the trade increases the likelihood of winning outcomes for both User 1, and 2. Each of User 1, and 2, appears receptive to a proposed trade—as indicated by mapping their current biometric state and team needs to trade risk tolerance, using the GMM of the full tensor space. The trade is proposed and accepted by Users 1 and 2.

The system considers the current state of each user and each team. There is no bias toward achieving a more positive outcome for any particular user. The system identifies trading combinations which should raise the likelihood of both trading partners having a winning outcome, i.e., the value of each trading partner's asset portfolio.

The real time evaluations are allocated to edge resources as they do not involve the calculation of tensor spaces or GMMs and do not require extensive computational resources. The real time activities map real time data using the GMMs, previously determined using the cloud resources, to identify real time trading opportunities. The use of real time data and the previously determined GMMs accounts for any shifts in player rankings or other variables which could alter the equivalence of two players, or combinations of players, with respect to any trading opportunities.

The methods described herein with regard to trading players among fantasy football league participants as users of method software are applicable to any set of traders/users in a market where assets are directly traded or swapped for other, hopefully equivalent assets. The disclosed methods provide a level field for all traders where overall performance is the target outcome and trades are proposed to optimize that goal.

Figure 1:
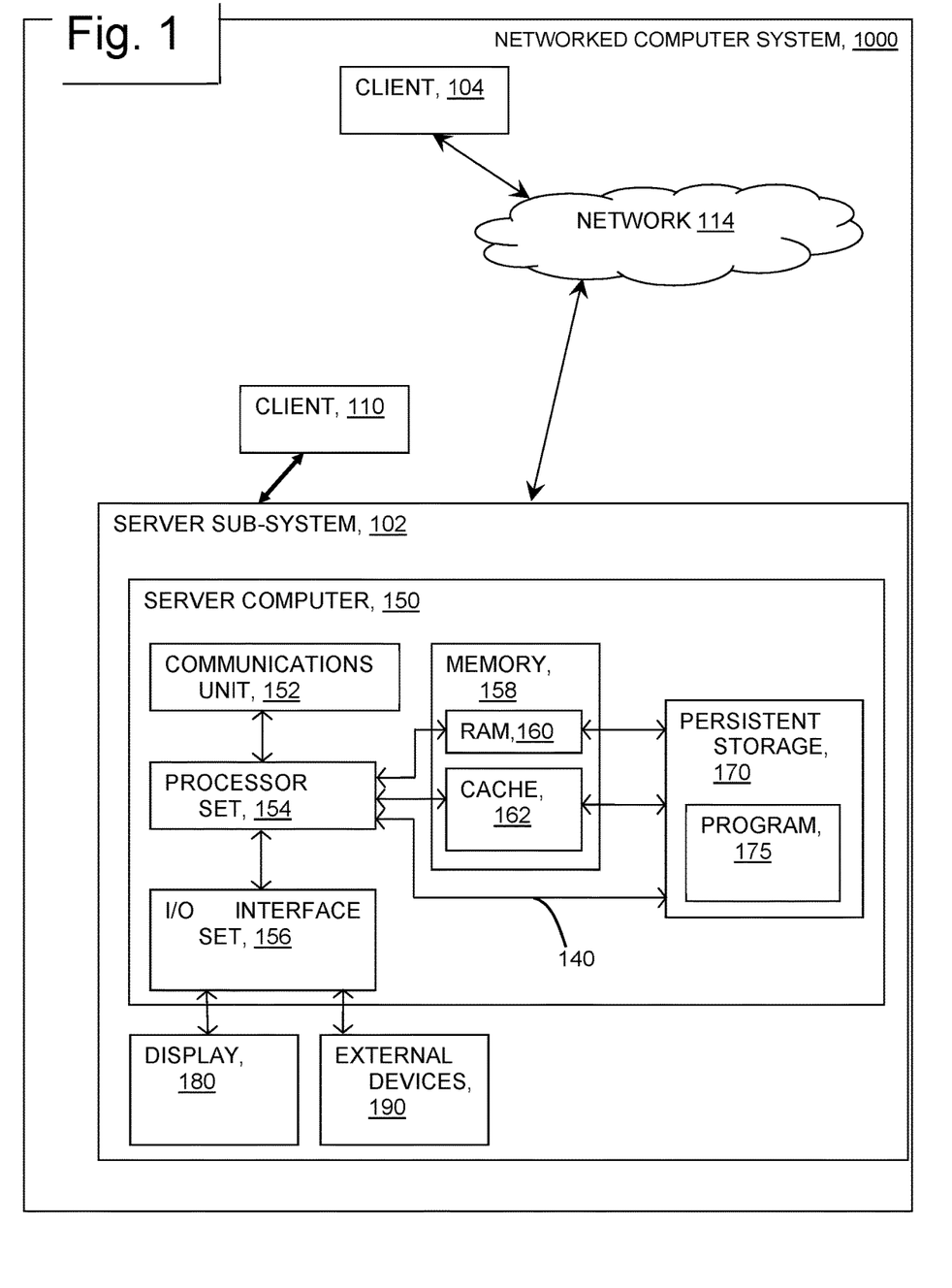
FIG. 1 provides a schematic illustration of a system, according to an embodiment of the invention.

FIG. 1 provides a schematic illustration of exemplary network resources associated with practicing the disclosed inventions. The inventions may be practiced in the processors of any of the disclosed elements which process an instruction stream. As shown in the figure, a networked Client device 110 connects wirelessly to server sub-system 102. Client device 104 connects wirelessly to server sub-system 102 via network 114. Client devices 104 and 110 comprise asset trading optimization program (not shown) together with sufficient computing resource (processor, memory, network communications hardware) to execute the program. As shown in FIG. 1, server sub-system 102 comprises a server computer 150. FIG. 1 depicts a block diagram of components of server computer 150 within a networked computer system 1000, in accordance with an embodiment of the present invention. It should be appreciated that FIG. 1 provides only an illustration of one implementation and does not imply any limitations with regard to the environments in which different embodiments can be implemented. Many modifications to the depicted environment can be made.

Server computer 150 can include processor(s) 154, memory 158, persistent storage 170, communications unit 152, input/output (I/O) interface(s) 156 and communications fabric 140. Communications fabric 140 provides communications between cache 162, memory 158, persistent storage 170, communications unit 152, and input/output (I/O) interface(s) 156. Communications fabric 140 can be implemented with any architecture designed for passing data and/or control information between processors (such as microprocessors, communications and network processors, etc.), system memory, peripheral devices, and any other hardware components within a system. For example, communications fabric 140 can be implemented with one or more buses.

Memory 158 and persistent storage 170 are computer readable storage media. In this embodiment, memory 158 includes random access memory (RAM) 160. In general, memory 158 can include any suitable volatile or non-volatile computer readable storage media. Cache 162 is a fast memory that enhances the performance of processor(s) 154 by holding recently accessed data, and data near recently accessed data, from memory 158.

Program instructions and data used to practice embodiments of the present invention, e.g., the asset trading resource optimization program 175, are stored in persistent storage 170 for execution and/or access by one or more of the respective processor(s) 154 of server computer 150 via cache 162. In this embodiment, persistent storage 170 includes a magnetic hard disk drive. Alternatively, or in addition to a magnetic hard disk drive, persistent storage 170 can include a solid-state hard drive, a semiconductor storage device, a read-only memory (ROM), an erasable programmable read-only memory (EPROM), a flash memory, or any other computer readable storage media that is capable of storing program instructions or digital information.

The media used by persistent storage 170 may also be removable. For example, a removable hard drive may be used for persistent storage 170. Other examples include optical and magnetic disks, thumb drives, and smart cards that are inserted into a drive for transfer onto another computer readable storage medium that is also part of persistent storage 170.

Communications unit 152, in these examples, provides for communications with other data processing systems or devices, including resources of client computing devices 104, and 110. In these examples, communications unit 152 includes one or more network interface cards. Communications unit 152 may provide communications through the use of either or both physical and wireless communications links. Software distribution programs, and other programs and data used for implementation of the present invention, may be downloaded to persistent storage 170 of server computer 150 through communications unit 152.

I/O interface(s) 156 allows for input and output of data with other devices that may be connected to server computer 150. For example, I/O interface(s) 156 may provide a connection to external device(s) 190 such as a keyboard, a keypad, a touch screen, a microphone, a digital camera, and/or some other suitable input device. External device(s) 190 can also include portable computer readable storage media such as, for example, thumb drives, portable optical or magnetic disks, and memory cards. Software and data used to practice embodiments of the present invention, e.g., asset trading resource optimization program 175 on server computer 150, can be stored on such portable computer readable storage media and can be loaded onto persistent storage 170 via I/O interface(s) 156. I/O interface(s) 156 also connect to a display 180.

Display 180 provides a mechanism to display data to a user and may be, for example, a computer monitor. Display 180 can also function as a touch screen, such as a display of a tablet computer.

Figure 2A:
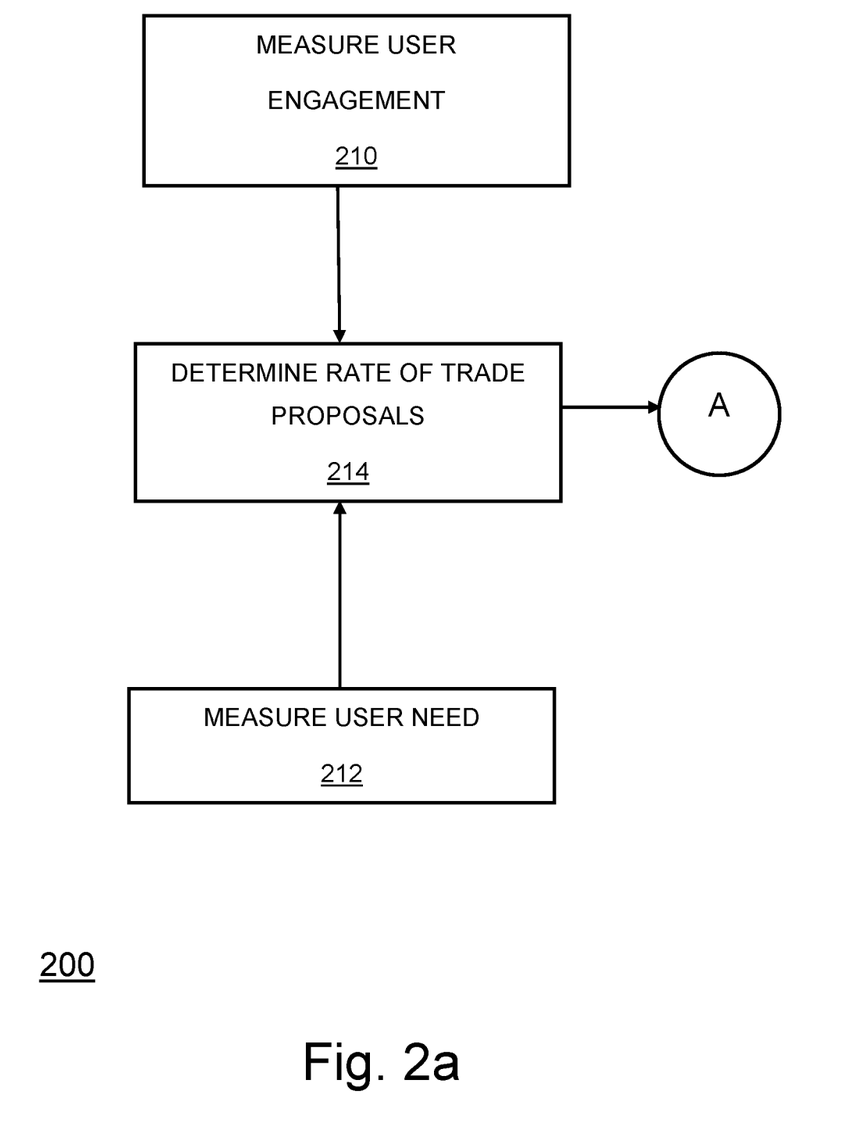
FIGS. 2*a*-2*c* provide a functional block diagram depicting an operational sequence, according to an embodiment of the invention.
Figure 2B:
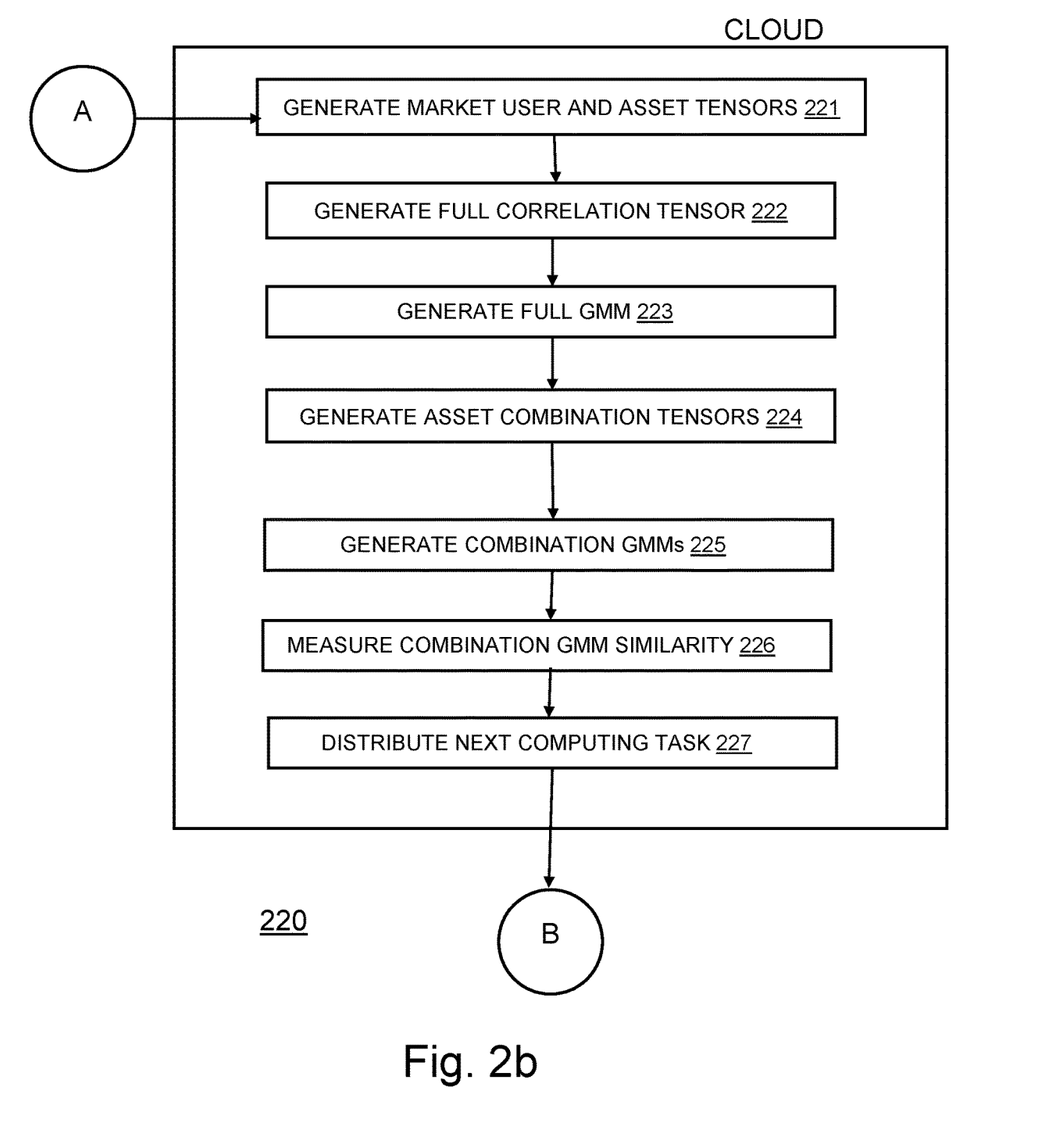
Figure 2C:
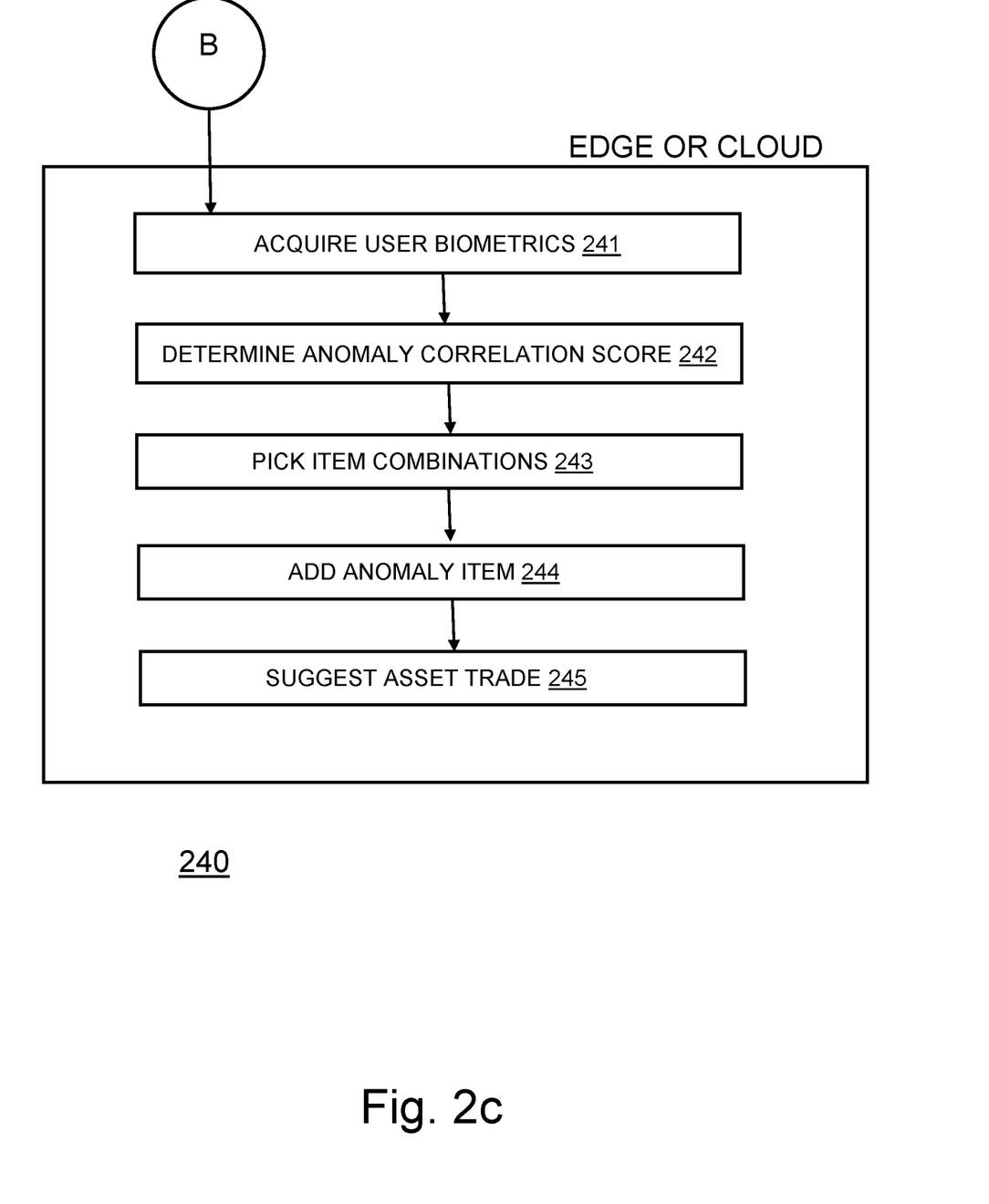

FIGS. 2a-2c provide combined flowcharts 200, 220, and 240 illustrating exemplary activities associated with the practice of the disclosed inventions. As shown in flowchart 200, after asset trading resource optimization program 175 start, the program measures user engagement at 210. Measurement of user engagement includes eye-tracking data from one or more user facing cameras of client computing devices 104 or 110. Engagement measures also include user application usage history in terms of number of sessions, session duration, and activity (mouse clicks, touchscreen interaction, and keyboard activity) during each session. In an embodiment, the method measures user engagement according to the number of players a user chooses to watch or subscribe to, both current team players and non-team players. The method can also consider user sessions with related software, e.g., league and player performance tracking software, when determining engagement levels, as well as user historic trading frequency. The method measures user engagement for each user across the entire set of users as well as over time, resulting in a set of snapshots of user engagement data for each of the set of users.

At 212, the method measures user needs. The method measures user needs across the set of users and over time resulting in a set of snapshots of user need. In an embodiment, the method measures user need in terms of current win/loss performance of the user's team relative to a league average performance. In this embodiment, the method evaluates individual user team players in terms of their performance relative to an average performance for their position. The method can also relate user need to the number of players a user chooses to watch, or subscribe to, both current team players and non-team players.

In an embodiment, the method uses measured user need and user engagement to determine the rate of trade proposals 214, a given user would be amenable to at any time. In this embodiment, the method determines the rate from need and engagement using iterative numerical evaluation methods, such as Runge-Kutta methods to determine relevant slopes in the data set associated with higher or lower trade receptivity based upon the independent variables for user need and engagement. In this embodiment, the method passes the determined rate of trade proposal data, as well as all user need and engagement data, to the next segment of the method at element A of flowchart 200.

In an embodiment, the tasks of flowchart 220, require extensive computing resources and the method allocates those tasks to cloud resources. As shown in FIG. 2b, the method passes the user data and determined trade rate to cloud resources. The method generates market asset and user tensors at 221. The user tensors include user engagement and need data, as well as user asset portfolio and portfolio performance data. The asset tensors include all data available regarding the traded asset, asset performance, trading history, descriptive data, etc. At 222, the method generates a matrix for the full tensor space correlating the user and asset tensor independent variables. This matrix can comprise millions, or billions, of rows and columns, necessitating the use of cloud resources. At 223 the method generates a Gaussian mix model (GMM) for the full tensor space, mapping the clusters of correlated data points as classes as well as providing a probability, or confidence level, for each data point and the mapped clusters/classes. The GMM indicates which correlations are present in the full tensor space and the probability indicates how well any particular data point maps to any selected class of correlations (e.g., how well a set of user data maps to a high receptivity for proposed trading).

At 224, the method generates one or more tensor spaces for combinations of assets. For a fantasy sports league, the combinations are an existing team with one or more current players traded for other available players. In the broader sense, the combinations are existing asset portfolios with one or more current assets exchanged for other assets. In an embodiment, the method considers only assets considered equivalent by some ranking available from the full tensor space GMM, e.g., only the exchange of players having a similar correlation to a winning outcome class, and/or a similar player weighting, are generated. In an embodiment, all potential player combinations are evaluated.

At 225, the method generates GMMs for the combination tensor space(s). The method maps the correlations between the independent variables of the tensor spaces, including the correlation between combinations of players and winning outcomes, using these GMMs. In an embodiment, the method ranks different combinations of players according to their sparseness (market class) with regard to the winning outcome, as well as the combination of their sparseness and their weight (market ranking). In this embodiment, the method uses the ranking of the different combinations from the GMMs to compare and identify similarly ranked combinations of players/assets at 226.

Trades can be optimized according to a function of market ranking (weight) and market class (sparseness). In an embodiment, the combined values of the market class—market ranking functions on each side of a trade must be similar or equal for the trade to be equitable to both traders.

At 227 the method distributes the next level of computing tasks. In an embodiment, the next level of computing tasks is the use of the previously generated GMMs to evaluate trading options using current, real time data. As this task requires fewer resources than tasks 221-226, the method distributes it to edge resources rather than cloud resources. The output of flowchart 220 is passed along at item B.

In an embodiment, as shown in flowchart 240 of FIG. 2c, at 241, the method acquires current user biometric data. In this embodiment, the method can limit the user biometric data to a single user, or can acquire current biometric data for all users. In this embodiment, the method can map the current data to a current trade rate value for each user with the full tensor space GMM. At 242, the method generates anomaly correlation scores for anomalous data points—those data points having a mis-match between their market ranking (weight) and their market class (sparseness). As an example, a lowly ranked player C, may correlate better with a winning outcome for User 1 than for the team the player is currently on, User 2. Current user data for each of User 1 and User 2, indicates that each user has similar receptivity to proposed trades according to the GMM for the full tensor. User 1's team would benefit from trading for player C. User 1's player D, has a similar market ranking as C, but adding D does not increase User 2's likelihood of a winning outcome. C for D is not an equitable trade and will not be proposed. At 243, the method considers the combination of C, and R, from User 2's team for the combination of D, and J, from User 1's team. These combinations have similar market rankings, and each increase the recipients' likelihood of a winning outcome. At 244 the anomaly item (C) is added to the proposed trade and the trade is suggested at 245.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 3:
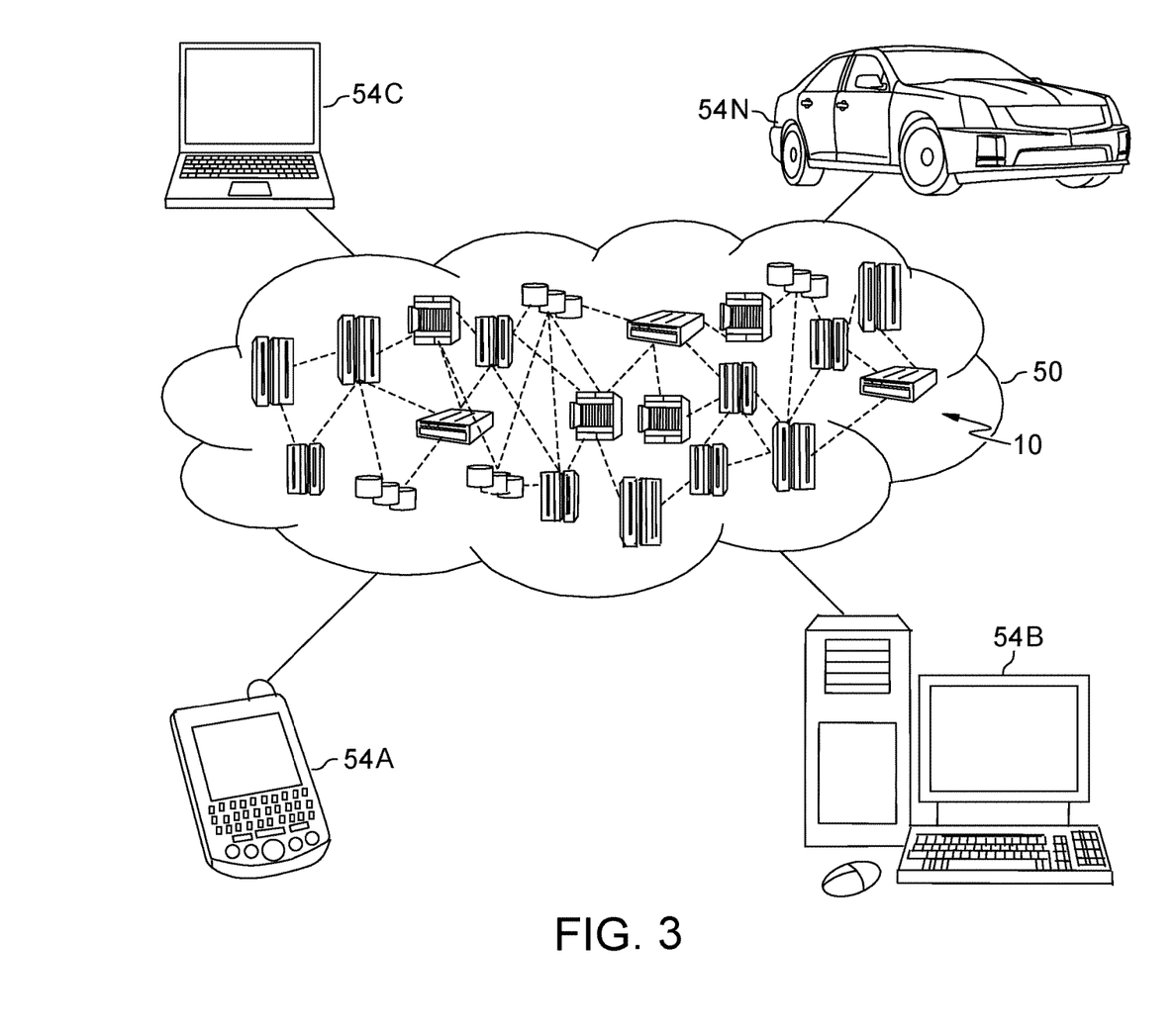
FIG. 3 depicts a cloud computing environment, according to an embodiment of the invention.

Referring now to FIG. 3, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 3 are intended to be illustrative only and that computing nodes 10 and cloud computing environment 50 can communicate with any type of computerized device over any type of network and/or network addressable connection (e.g., using a web browser).

Figure 4:
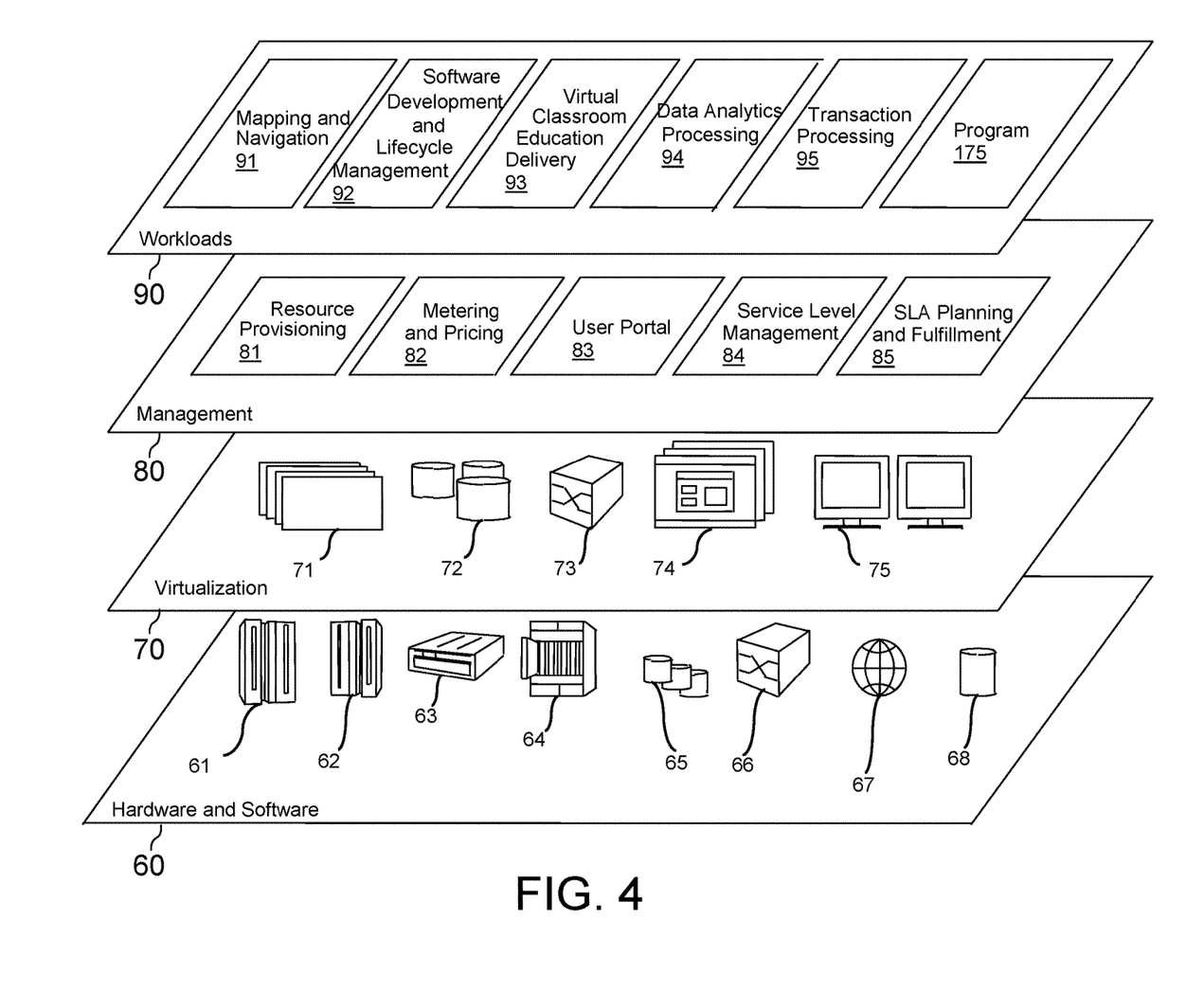
FIG. 4 depicts abstraction model layers, according to an embodiment of the invention.

Referring now to FIG. 4, a set of functional abstraction layers provided by cloud computing environment 50 (FIG. 3) is shown. It should be understood in advance that the components, layers, and functions shown in FIG. 4 are intended to be illustrative only and embodiments of the invention are not limited thereto. As depicted, the following layers and corresponding functions are provided.

Hardware and software layer 60 includes hardware and software components. Examples of hardware components include: mainframes 61; RISC (Reduced Instruction Set Computer) architecture-based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and asset trading resource optimization program 175.

The present invention may be a system, a method, and/or a computer program product at any possible technical detail level of integration. The invention may be beneficially practiced in any system, single or parallel, which processes an instruction stream. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A computer implemented method for managing application execution, the method comprising:

generating a first tensor space associated with market assets, by a cloud resource;

generating a second tensor space associated with users, by a cloud resource;

allocating a generation of a combined tenor space from the first tensor space and the second tensor space to cloud resources according to a magnitude of the computational problem;

generating a combined tensor space from the first tensor space with the second tensor space using cloud resources;

allocating a mapping of correlations between the market assets and positive user outcomes to cloud resources according to a magnitude of the computational problem;

mapping correlations between the market assets and positive user outcomes, within the combined tensor space;

allocating a determination of market asset allocation opportunities according to the correlations to edge cloud resources according to a magnitude of the computational problem;

determining market asset allocation opportunities according to the correlations; and suggesting market asset allocations according to a user risk assessment.

2. The computer implemented method according to claim 1, further comprising:

allocating computing tasks according to a factor selected from the group consisting of: matrix density, data location, and edge asset capacity.

3. The computer implemented method according to claim 1, wherein a rate of suggesting market asset allocations is determined according to an assessment of user risk tolerance.

4. The computer implemented method according to claim 1, wherein mapping correlations associated with the market assets and positive user outcomes within the combined tensor space comprises calculating Gaussian mix models for tensor spaces.

5. The computer implemented method according to claim 4, further comprising comparing Gaussian mix models of the tensor spaces.

6. The computer implemented method according to claim 1, further comprising:

acquiring user biometric data; and suggesting market asset allocations according to the user biometric data.

7. The computer implemented method according to claim 1, wherein market asset correlations include market ranking and market class factors.

8. A computer program product for managing application execution, the computer program product comprising one or more computer readable storage devices and stored program instructions on the one or more computer readable storage devices, the stored program instructions comprising:

program instructions for generating a first tensor space associated with market assets by a cloud resource;

program instructions for generating a second tensor space associated with users, by a cloud resource;

program instructions for allocating a generation of a combined tenor space from the first tensor space and the second tensor space to cloud resources according to a magnitude of the computational problem;

program instructions for generating a combined tensor space from the first tensor space with the second tensor space using cloud resources;

program instructions for allocating a mapping of correlations between the market assets and positive user outcomes to cloud resources according to a magnitude of the computational problem;

program instructions for mapping correlations between the market assets and positive user outcomes, within the combined tensor space;

program instructions for allocating a determination of market asset allocation opportunities according to the correlations to edge cloud resources according to a magnitude of the computational problem;

program instructions for determining market asset allocation opportunities according to the correlations; and program instructions for suggesting market asset allocations according to a user risk assessment.

9. The computer program product according to claim 8, further comprising program instructions for allocating computing tasks according to a factor selected from the group consisting of: matrix density, data location, and edge asset capacity.

10. The computer program product according to claim 8, further comprising program instructions for determining a rate of suggesting market asset allocations according to an assessment of user risk tolerance.

11. The computer program product according to claim 8, wherein mapping correlations associated with the market assets and positive outcomes within the combined tensor space comprises calculating Gaussian mix models for tensor spaces.

12. The computer program product according to claim 11, further comprising program instructions for comparing the Gaussian mix models of the tensor space.

13. The computer program product according to claim 8, further comprising program instructions for: acquiring user biometric data; and suggesting market asset allocations according to the user biometric data.

14. The computer program product according to claim 8, wherein market asset correlations include market ranking and market class factors.

15. A computer system for managing application execution, the computer system comprising:
one or more computer processors;
one or more computer readable storage devices; and
stored program instructions on the one or more computer readable storage devices for execution by the one or more computer processors, the stored program instructions comprising:
program instructions for generating a first tensor space associated with market assets by a cloud resource;
program instructions for generating a second tensor space associated with users, by a cloud resource;
program instructions for allocating a generation of a combined tenor space from the first tensor space and the second tensor space to cloud resources according to a magnitude of the computational problem;
program instructions for generating a combined tensor space from the first tensor space with the second tensor space using cloud resources;
program instructions for allocating a mapping of correlations between the market assets and positive user outcomes to cloud resources according to a magnitude of the computational problem;
program instructions for mapping correlations between the market assets and positive user outcomes, within the combined tensor space;
program instructions for allocating a determination of market asset allocation opportunities according to the correlations to edge cloud resources according to a magnitude of the computational problem;
program instructions for determining market asset allocation opportunities according to the correlations; and
program instructions for suggesting market asset allocations according to a user risk assessment.

16. The computer system according to claim 15, further comprising program instructions for allocating computing tasks according to a factor selected from the group consisting of: matrix density, data location, and edge asset capacity.

17. The computer system according to claim 15, further comprising program instructions for determining a rate of suggesting market asset allocations according to an assessment of user risk tolerance.

18. The computer system according to claim 15, wherein mapping correlations associated with the market assets and positive outcomes within the combined tensor space comprises calculating Gaussian mix models for tensor spaces.

19. The computer system according to claim 18, further comprising program instructions for comparing the Gaussian mix models of the tensor spaces.

20. The computer system according to claim 15, further comprising program instructions for: acquiring user biometric data; and suggesting market asset allocations according to the user biometric data.

* * * * *